United States Patent
Wei et al.

(10) Patent No.: US 11,067,579 B2
(45) Date of Patent: Jul. 20, 2021

(54) TARGET MARKER GP73 FOR DETECTING STEATOHEPATITIS AND DETECTION APPLICATION METHOD

(71) Applicants: BEIJING DITAN HOSPITAL CAPITAL MEDICAL UNIVERSITY, Beijing (CN); BEIJING HOTGEN BIOTECH CO., LTD, Beijing (CN)

(72) Inventors: Hongshan Wei, Beijing (CN); Boan Li, Beijing (CN); Changqing Lin, Beijing (CN); Yong Qiao, Beijing (CN)

(73) Assignees: BEIJING DITAN HOSPITAL CAPITAL MEDICAL UNIVERSITY, Beijing (CN); BEIJING HOTGEN BIOTECH CO., LTD, Beijing (CN)

( * ) Notice: Subject to any disclaimer, the term of this patent is extended or adjusted under 35 U.S.C. 154(b) by 0 days.

(21) Appl. No.: 16/638,713

(22) PCT Filed: Jun. 19, 2017

(86) PCT No.: PCT/CN2017/088945
§ 371 (c)(1),
(2) Date: Feb. 12, 2020

(87) PCT Pub. No.: WO2018/227643
PCT Pub. Date: Dec. 20, 2018

(65) Prior Publication Data
US 2020/0217846 A1    Jul. 9, 2020

(30) Foreign Application Priority Data

Jun. 13, 2017  (CN) .......................... 201710443740.6

(51) Int. Cl.
*G01N 33/53*    (2006.01)
*G01N 33/576*   (2006.01)

(52) U.S. Cl.
CPC ... *G01N 33/5767* (2013.01); *G01N 2800/085* (2013.01)

(58) Field of Classification Search
None
See application file for complete search history.

(56) References Cited

U.S. PATENT DOCUMENTS

2004/0241744 A1* 12/2004 Kohno ................... G01N 33/92
                                                         435/7.1
2010/0184049 A1*  7/2010 Goodison ............ C12Q 1/6886
                                                        435/6.11

OTHER PUBLICATIONS

Torzewski et al., Animal Models of C-Reactive Protein, Hindawl Publishing Corporation, Mediators of Inflammation, vol. 2014, 2014, pp. 1-7. (Year: 2014).*
Van Der Vekiens et al., Human and equine cardiovascular endocrinology: beware to compare, Cardiovascular Endocrinology 2013, vol. 2, No. 4, pp. 67-76. (Year: 2013).*
Wei et al., Serum GP73 were increased in patients with fatty liver disease, Chinese J Exp Clin Virol, Aug. 2013, vol. 27, No. 4, pp. 244-246. (Year: 2013).*
Wei et al., GP73 is a potential marker for evaluating AIDS progression and antiretroviral therapy efficacy, Mol Biol Rep, 2013, 40: pp. 6397-6405. (Year: 2013).*

* cited by examiner

*Primary Examiner* — Gary Counts
(74) *Attorney, Agent, or Firm* — Hauptman Ham, LLP

(57) ABSTRACT

A novel serological target marker GP73 used for diagnosing and identifying a simple fatty liver and steatohepatitis in populations with fatty liver and a detection application method thereof. The serological target marker GP73 and the application thereof can replace golden standard liver puncture to identify and diagnose the simple fatty liver and steatohepatitis in populations with fatty liver, reduce the detection pain of a patient, and have an extremely high clinical application value in clinically identifying and diagnosing the simple fatty liver and steatohepatitis in the populations with fatty liver and assisting the treatment of the simple fatty liver and steatohepatitis.

7 Claims, 6 Drawing Sheets

|  |  | Clinical Background | | |
| --- | --- | --- | --- | --- |
|  |  | Simple fatty liver | Steatohepatitis | Total |
| GP73 Detection Results by Beijing Hotgen Biotech Co., Ltd., Cut-off = 82.25 ng/ml | Simple fatty liver | 119 | 9 | 128 |
| | Steatohepatitis | 18 | 54 | 72 |
| | Total | 137 | 63 | 200 |
| | Coincidence Rate | 86.86% | 85.71% | 86.50% |

TARGET MARKER GP73 FOR DETECTING STEATOHEPATITIS AND DETECTION APPLICATION METHOD

RELATED APPLICATIONS

The present application is a National Phase of International Application Number PCT/CN2017/088945, filed Jun. 19, 2017, and claims the priority of China Application No. 201710443740.6, filed Jun. 13, 2017.

TECHNICAL FIELD

The present invention relates to a novel marker and a detection method for detecting steatohepatitis in vitro, and belongs to the subfield of biotechnology and in vitro diagnosis.

BACKGROUND

Fatty liver refers to a disease in which there is excessive abnormal accumulation of fat in liver cells due to various reasons. Normal human liver tissue contains a small amount of fat, and the weight thereof accounts for about 4% to 5% of the weight of the liver. If the amount of fat exceeds 5%, it is mild fatty liver; if the amount of fat exceeds 10%, it is moderate fatty liver, and if the amount of fat exceeds 25%, it is severe fatty liver. Fatty liver is currently one of the most common chronic liver diseases, with an incidence rate of more than 30% in developed countries and some developing countries. It has become an important public health problem and seriously threatens the health of people. Fatty liver includes the main pathological stages of a simple fatty liver, steatohepatitis, liver fibrosis, liver cirrhosis and so on; among those stages of fatty liver, a simple fatty liver is benign, and can be reversed through diet, exercise regulation and the like, without the need for specific treatment; however, if steatohepatitis is not treated in time, it will develop into liver fibrosis, liver cirrhosis, and liver cancer as the disease progresses; it is reported that the incidence rate of steatohepatitis converting to liver fibrosis, liver cirrhosis, finally to liver cancer is equivalent to the incidence rate of viral hepatitis. Steatohepatitis is a serious threat to the health of people. At present, fatty liver is mainly detected by B-mode ultrasound, CT, MM and other imaging means, but imaging detection cannot distinguish between a simple fatty liver and steatohepatitis. The diagnosis of steatohepatitis still depends on liver puncture detection, which will bring great physical and psychological burden to patients, and is not conducive to the diagnosis and daily detection of steatohepatitis.

Golgi protein 73 (hereinafter referred to as GP73 unless otherwise specified) is a Golgi glycoprotein, and a novel transmembrane glycoprotein first discovered in 2000 by Kladney et al. in the study of the etiology of adult giant cell hepatitis. It is also known as type II Golgi membrane protein (Golph 2) and Golgi membrane protein I (Golm 1), and has a relative molecular weight of 73,000 kDa. GP73 is not expressed or expressed in a small amount in normal liver cells. Studies in recent years have found that GP73 is highly expressed in a variety of liver diseases such as liver fibrosis, liver cirrhosis, and liver cancer, and can be secreted into serum; an increase of GP73 is most obvious in patients with liver cancer, so GP73 is one of the preferred markers for early diagnosis of liver cancer, and the sensitivity and specificity thereof are better than those of AFP.

Chinese Patent Publication CN 101735319 A (BEIJING HOTGEN BIOTECH CO LTD, patent name "Monoclonal antibody against GP73 protein, preparation method and application thereof") discloses a monoclonal antibody against Golgi protein 73, i.e., GP73, and an enzyme-linked immunological quantitative detection kit and a rapid diagnostic kit employing advantage of GP73; and discloses that the critical value of GP73 content for distinguishing between normal people and patients with liver diseases is 40 ng/ml, and that the critical value of GP73 content for distinguishing between patients with benign liver diseases and patients with malignant liver diseases is 100 ng/ml.

Chinese Patent Publication CN 101407544 A (Patent Name: "Anti-Golgi apparatus protein monoclonal antibody and use") discloses an anti-GP73 monoclonal antibody, an enzyme immunoreagent for liver cancer detection using the monoclonal antibody, and applications thereof in immunoprecipitation, immunoblotting, immunohistochemistry and the like.

Chinese Patent Publication CN 104215761 A (patent name: "Kit for detecting anti-GP73 antibody in serum") discloses an enzyme-linked immunoassay kit for detecting an anti-GP73 antibody in serum, which is mainly used for liver cancer detection.

In recent years, studies on GP73 and related applications thereof mainly focus on the field of early diagnosis of liver cancer, and GP73-related patent applications also mainly focus on the field of in vitro diagnostic kits for the detection of liver cancer employing GP73 and antibodies thereof. And there is neither reports on studies and applications of, nor related patent applications for GP73 being employed for diagnosis and identification of a simple fatty liver and steatohepatitis in populations with fatty liver. After studying and analyzing a large number of clinical samples, we have sufficient proof that GP73 is an excellent serological marker for diagnosis and identification of a simple fatty liver and steatohepatitis in populations with fatty liver, and it has important clinical application value for both diagnosis and identification for populations with steatohepatitis.

SUMMARY OF THE INVENTION

Currently, liver puncture is used clinically to diagnose and identify a simple fatty liver and steatohepatitis in populations with fatty liver, which brings great pain to patients. In order to overcome the deficiency in the existing imaging and serological detection techniques that they cannot diagnose and identify a simple fatty liver and steatohepatitis in populations with fatty liver, the present invention provides a novel serological target marker GP73 for diagnosing and identifying a simple fatty liver and steatohepatitis in populations with fatty liver, and further provides a detection kit for detecting GP73, a detection method and the determination criteria thereof for diagnosis and identification of a simple fatty liver and steatohepatitis in populations with fatty liver.

The present invention provides a novel serological target marker GP73 for diagnosing and identifying a simple fatty liver and steatohepatitis in populations with fatty liver, and an in vitro diagnosis method for detecting the content of GP73 in test samples.

The present invention further provides a serological in vitro diagnosis detection kit for diagnosing and identifying a simple fatty liver and steatohepatitis in populations with fatty liver, a method for detecting GP73 by using the in vitro diagnosis detection kit, and the determination criteria thereof.

In the embodiments of the present invention, the principle of the GP73 detection method is the principle of immunological detection methods based on an antigen-antibody binding reaction, and the method is preferably any one of chemiluminescence, enzyme-linked immunoassay, and immunochromatography.

In some embodiments of the present invention, the chemiluminescence is at least one of chemiluminescence, magnetic particle-based chemiluminescence, electrochemiluminescence, enzymatic chemiluminescence, and time-resolved chemiluminescence.

In some embodiments of the present invention, the enzyme-linked immunoassay is at least one of enzyme-linked immunosorbent assay, immunofiltration assay, and protein chip.

In some embodiments of the present invention, the immunochrom atography is at least one of up-conversion luminescence immunochromatography, latex immunochromatography, colloidal gold immunochromatography, luminescence immunochromatography, and quantum dot immunochromatography.

In some embodiments of the present invention, the GP73 test sample is a blood sample from populations with fatty liver, and the test result of the blood sample is used for diagnosing and identifying a simple fatty liver and steatohepatitis in populations with fatty liver.

In some embodiments of the present invention, the determination cutoff value of the GP73 serological in vitro diagnosis detection kit for diagnosing and identifying a simple fatty liver and steatohepatitis in populations with fatty liver is 82.25 ng/ml.

Compared with the prior art, the present invention provides a novel serological target marker GP73 for diagnosing and identifying a simple fatty liver and steatohepatitis in populations with fatty liver, and further provides a GP73 detection method for diagnosing and identifying a simple fatty liver and steatohepatitis in populations with fatty liver, and the determination criteria thereof, which solve the problem that the existing imaging and serological detection techniques cannot diagnose and identify a simple fatty liver and steatohepatitis in populations with fatty liver, and provide a basis for diagnosis and treatment of steatohepatitis; the present invention adopts a blood sample as the test sample, which greatly reduces the pain of patients caused by detecting steatohepatitis through liver puncture; and thus the present invention has important clinical diagnostic value and clinical significance for identifying a simple fatty liver and steatohepatitis in populations with fatty liver.

DETAILED DESCRIPTION

Figure 1:
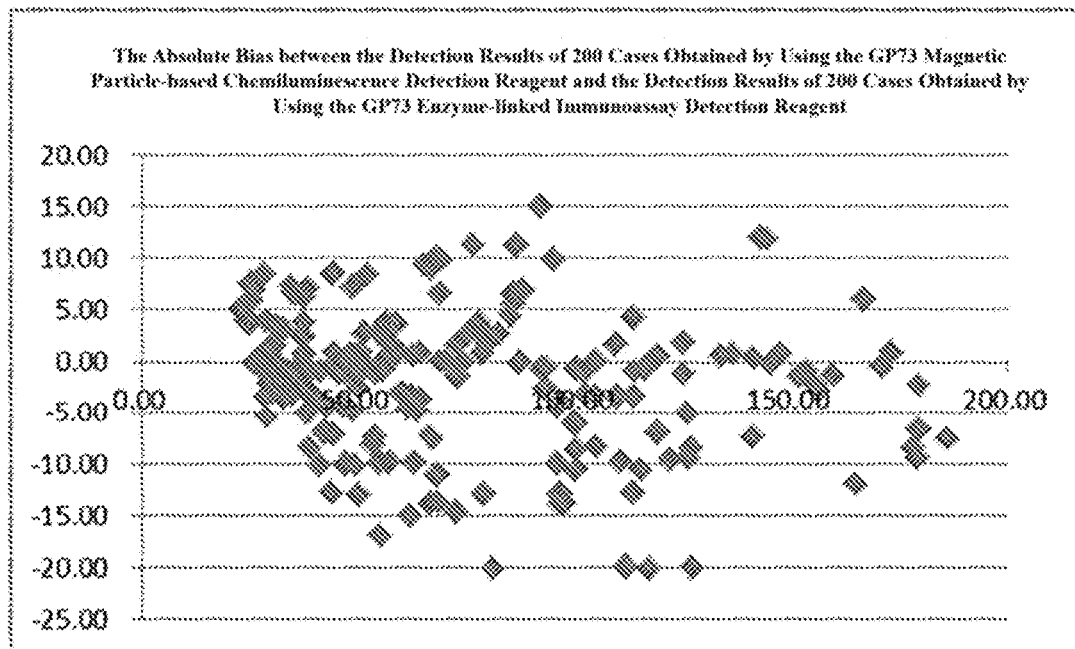
FIG. 1 is a diagram showing the absolute bias between the detection results of 200 cases obtained by using the GP73 magnetic particle-based chemiluminescence detection reagent and the detection results of 200 cases obtained by using the GP73 enzyme-linked immunoassay detection reagent.

The present invention will be further described below with reference to the drawings and Examples. It should be understood that the preferred examples described herein are merely illustrative of the present invention and do not limit the scope of the invention.

It is to understand that the terminology used herein is for the purpose of describing particular embodiments only, and is not intended to limit the present invention. Where a range of values is provided in the present invention, it is understood that each intervening value between the upper and lower limits of that range is also specifically disclosed. Each smaller range between any stated value or intervening value in a stated range and any other stated value or intervening value in that stated range is encompassed within the present invention. The upper and lower limits of these smaller ranges may independently be included or excluded in the range.

Unless defined otherwise, all technical and scientific terms used herein have the same meaning as commonly understood by one of ordinary skill in the art to which this invention belongs. Although only preferred experimental, assay or test methods are described herein, any method similar or equivalent to those described herein can be used in the experiments, assays or tests of the present invention. All documents mentioned in this specification are incorporated by reference to disclose and describe methods or experiments related to said documents. In the event of conflict with any incorporated document, this specification shall prevail.

In the present invention, noun terms include both singular and plural forms, unless the context clearly indicates otherwise. The expression "at least one" or "at least one kind" mentioned in the present invention is not only intended to include the case of "one" or "one kind", but also more importantly include the case of "multiple" or "multiple kinds".

The present invention provides a GP73 target marker, a method for detecting GP73 and the determination criteria thereof, wherein the anti-GP73 protein antibody was applied to prepare a detection reagent working on the principle of immunological detection methods based on an antigen-antibody binding reaction, including a quantitative detection reagent of any one of chemiluminescence, enzyme-linked immunoassay, immunochromatography and methods improved based on the foregoing methods; the sample detected by using the quantitative reagent is a blood sample from populations with fatty liver, and may be any one of serum, plasma, and whole blood; the detection result of the blood sample is used for diagnosing and identifying a simple fatty liver and steatohepatitis in populations with fatty liver.

The method of measuring GP73 in the present invention includes using reagents including, but not limited to, antibodies. The antibodies specifically include monoclonal antibodies (including full-length monoclonal antibodies), polyclonal antibodies, multi-specific antibodies (e.g., bispecific antibodies), and antibody fragments, such as variable domains and other portions in antibodies that exhibit desired biological activity. The term "monoclonal antibody (mAb)" refers to an antibody that is highly specific and is directed against a single antigenic determinant (epitope). Thus, the term "monoclonal" refers to antibodies directed against the same epitope, and should not be construed as the production of the antibodies requiring any particular method. It should be understood that monoclonal antibodies can be prepared by any technique or method known in the art, including, for example, the hybridoma method (Kohler et al., 1975, Nature 256: 495), or the recombinant DNA method known in the art (for example, see U.S. Pat. No. 4,816,567), or a method for producing monoclonal antibodies in a recombinant manner by using a phage antibody library and by using the techniques described in the following literature for separation: Clackson et al., 1991, Nature 352: 624-628; and Marks et al., 1991, J. Mol. Biol. 222: 581-597.

In the present invention, the "antibody fragment" refers to a molecule different from an intact antibody, which comprises a portion of the intact antibody and binds to an antigen to which the intact antibody binds. Examples of antibody fragments include, but are not limited to, Fv, Fab, Fab', Fab'-SH, and F(ab')2; diabodies; linear antibodies; single chain antibody molecules (e.g., scFv); and multi-specific antibodies formed from antibody fragments.

The reagents according to the present invention also include other reagents. Examples of the other reagents include an ABC diluent, a TMB chromogen solution, a TMB stop solution, a wash solution, and the like. In some embodiments, any one of the above substances may be stored separately in different containers (e.g., vials) in a state of being separated from the other substances, as long as they can be in contact with each other at the time of use. In addition, it is preferable that any two or more of the above substances may be mixed to exist as a mixture.

In certain embodiments, the other reagents may be provided respectively in the form of a dry powder, or in the form of a solution, such as in the form of an aqueous solution. In the case that they are respectively present in the form of an aqueous solution, the concentration or content of each of these substances can be easily determined by those skilled in the art according to different needs. For example, for storage purposes, the concentration of the substance may be high. When the substance is in working state or in use, the concentration may be reduced to a working concentration by, for example, diluting the above-mentioned solution with a high concentration.

In the present invention, a reagent for measuring GP73 may be further prepared as a diagnostic agent for identifying a simple fatty liver and steatohepatitis in a subject with fatty liver. The diagnostic agent may be in the form of a diagnostic composition, a diagnostic kit, or any other forms in which a plurality of reagents that are present separately are used in combination.

Example 1

Preparation of anti-GP73 protein antibody: The anti-GP73 protein antibody was prepared with reference to existing patented technologies, or selected from commercially available ones, or prepared by generally known technologies, and the prepared or selected monoclonal antibody can be used for accurate quantitative detection and determination of GP73 in blood samples from populations with fatty liver.

To better explain the present invention, the anti-GP73 protein antibody described in certain embodiments of the present invention is preferably the anti-GP73 protein antibody prepared by the anti-GP73 protein antibody preparation method in the patented technology of BEIJING HOTGEN BIOTECH CO LTD, CN 101735319 B, "Monoclonal antibody against GP73 protein, preparation method and application thereof", and the hybridoma cell line (3E12 strain) for preparing the anti-GP73 protein antibody was deposited under the deposit number CGMCC No. 2742 on Nov. 11, 2008 in the China General Microbiological Culture Collection Center (CGMCC).

Preparation of monoclonal antibody: Adult BALB/c mice were inoculated intraperitoneally with pristane or liquid paraffin, 0.3 to 0.5 ml per mouse; 7 to 10 days later, the mice were inoculated intraperitoneally with the hybridoma cell line, 3E12 strain which had been diluted with PBS or serum-free medium, $5 \times 10^5/0.2$ ml per mouse; ascitic fluid production in the mice was observed every day; if the abdomens were significantly enlarged and the skins felt tense when touched by hand, ascitic fluid could be collected, about 3 ml of ascitic fluid was collected per mouse; the ascitic fluid was centrifuged at 2000 r/min for 5 minutes to remove cell components and other precipitates; the supernatant was collected and purified by a recombinant protein G pre-packed chromatography column to obtain the anti-GP73 monoclonal antibody.

Example 2

Preparation of chemiluminescence detection reagent: The chemiluminescence is at least one of chemiluminescence, magnetic particle-based chemiluminescence, electrochemiluminescence, enzymatic chemiluminescence, time-resolved chemiluminescence, and improved methods thereof. Those different chemiluminescence methods are different only in labeling particle and separation method, but they share the same reaction principle. After being subjected to anti-GP73 protein antibody concentration optimization treatment, those methods all can realize accurate quantitative detection and identification of a simple fatty liver and steatohepatitis in populations with fatty liver, and achieve the purpose of auxiliary diagnosis and treatment of steatohepatitis. The preparation of those GP73 chemiluminescence methods comes from mature chemiluminescence preparation technologies, and those technologies were optimized to achieve excellent detection results.

In order to better explain the present invention, in certain embodiments of the present invention, the chemiluminescence used for preparing the chemiluminescence detection reagent was preferably magnetic particle-based chemiluminescence, the magnetic particle-based chemiluminescence detection reagent was prepared with reference to the method disclosed in the related patented technology of BEIJING HOTGEN BIOTECH CO LTD, and the antibody was the anti-GP73 protein antibody described in Example 1.

1. Preparation of GP73 separation reagent for GP73 magnetic particle-based chemiluminescence detection reagent In summary, the preparation of the GP73 separation reagent was as follows: magnetic particles were reacted with the anti-GP73 protein antibody to form a conjugate, which was added at a certain concentration into a buffer to prepare the separation reagent. The main steps were as follows:

After magnetic beads were uniformly mixed, a magnetic field was added to remove the supernatant; the magnetic beads were washed once with a coating buffer, then an activator (carbodiimide) was added thereto, and the solution was oscillated for reaction at room temperature for 30 minutes; the supernatant was then removed, the coating buffer and an appropriate amount of the anti-GP73 protein antibody were added thereto, and oscillation was conducted at room temperature for 3 hours; after the reaction was completed, a blocking buffer was added and oscillation was conducted; lastly, a wash solution was added, and after the washing was completed, a preservation liquid was added to preserve overnight.

The coating buffer was a 0.1 mol/L MES buffer at pH 5.0.

The final concentration of the activator carbodiimide was 0.01 to 0.1 g/ml.

The appropriate concentration of the anti-GP73 protein antibody was 10 to 100 ug/mg magnetic beads.

After the coating was completed, a magnetic field was added to discard the supernatant, a blocking buffer having a volume of about 10 times the volume of the mixed solution was added, and the resultant was oscillated at room temperature for at least 1 hour.

The main components of the blocking buffer included a 50 mM Tris buffer, a 1 to 5% BSA solution, and a 0.1% preservative, and the pH of the blocking buffer was 7.4.

After the blocking was completed, a magnetic field was added to discard the supernatant, and a wash solution having a volume of about 10 times the volume of the mixed solution was added for washing.

The main components of the wash solution included a 0.02 M PBS, a 100 nM sodium chloride solution, and a 0.5 to 1% TWEEN®-20 solution (Polysorbate 20).

After the washing was completed, a magnetic field was added to discard the supernatant, and a magnetic particle preservation liquid having a volume of exact 10 times the volume of the mixed solution was added to preserve the magnetic particles of the anti-DCP monoclonal antibody, thereby giving the GP73 separation reagent.

The main components of the preservation liquid included a 0.02 to 0.1 M PBS solution, a 1% to 5% BSA solution, a 0.1% preservative, and a 0.5 to 3% glycine solution, and the pH of the preservation liquid was 7.4.

2. Preparation of detection reagent for GP73 magnetic particle-based chemiluminescence detection reagent In summary, the preparation of the detection reagent was as follows: an alkaline phosphatase-labeled anti-GP73 protein antibody was added at a certain concentration into a buffer to prepare the detection reagent.

In order to better explain the present invention and correspond to the coated antibody, the alkaline phosphatase-labeled antibody was preferably an anti-GP73 protein antibody; and the preparation method was merely illustrative of the present invention, and should not be considered as a limitation on the preparation and use of the labeled antibody.

Alkaline phosphatase was taken so that the mass ratio of alkaline phosphatase to anti-GP73 protein antibody was 1/4 to 1/1, $NaIO_4$ (12.8 mg/ml, 4° C.) having the same volume as that of the alkaline phosphatase solution was added, and the reaction took place in the dark at 4° C. for 30 minutes; then an ethylene glycol solution having the same volume as that of the alkaline phosphatase solution was added, and the reaction took place in the dark at 4° C. for 45 minutes; the anti-GP73 protein antibody was added, then a CBS-labeled buffer (0.05 mol/L, pH 9.6) having a volume of 1/40 to 1/10 the volume of the mixed solution was added, and the resultant was dialyzed in the dark at 4° C. overnight; lastly, an ammonium sulfate solution was added to react for 2 hours; the obtained solution was centrifuged, the supernatant was discarded, and the precipitate was dissolved in a 0.01 mol/L PBS; thereafter, the solution was placed at 4° C. in the dark for dialysis overnight; after dialysis, an equal volume of glycerin was added, the solution was mixed uniformly and then stored at −20° C.

The alkaline phosphatase-labeled anti-GP73 protein antibody was added in a certain ratio (recommended concentration≥1:1000) into the preservation liquid, and the solution was mixed uniformly to give the GP73-labeled antibody, which is the prepared detection reagent.

3. Preparation of wash solution for GP73 magnetic particle-based chemiluminescence detection reagent The main components of the wash solution included a 0.1 M Tris buffer, a 0.1 to 1% TWEEN® solution (Polysorbate 20), and a 0.1% preservative.

4. Preparation of calibration solution for GP73 magnetic particle-based chemiluminescence detection reagent In summary, the preparation of the GP73 calibration solution was as follows: the GP73 antigen that passed inspection was added into a calibration production diluent, and the resultant was lyophilized to prepare the calibration solution.

The calibration production diluent included a 1 to 5% BSA solution, a 1 to 5% trehalose solution, and a 10 to 50% newborn bovine serum solution. The high-value GP73 antigen lyophilized solution was subjected to gradient dilution until it was diluted to an appropriate concentration. After detection, it was placed in a lyophilizer for lyophilization, wherein the pre-freezing time was 2 hours and the vacuumizing time was 16 to 24 hours.

5. Preparation of GP73 magnetic particle-based chemiluminescence detection reagent The GP73 separation reagent, the GP73 detection reagent, the GP73 wash solution, and the GP73 substrate solution, according to the requirements of the technological procedure or instructions, were respectively packaged into reagent bottles of corresponding size, or into the corresponding hole positions in the reagent strip of a strip-packaged reagent, and then sealed. The respectively packaged reagents, together with the calibration solution, a consumable reaction tank, a disposable sampling head, etc. constitute the GP73 magnetic particle-based chemiluminescence detection reagent, and the reagent is suitable for use with the automatic immunoassay analyzer of MQ60 series of BEIJING HOTGEN BIOTECH CO LTD.

Example 3

Preparation of GP73 enzyme-linked immunoassay detection reagent (for 96 persons): The enzyme-linked immunoassay is at least one of enzyme-linked immunosorbent assay, dot immunofiltration assay, magnetic particle-based enzyme-linked immunoassay, enzyme-linked immunofluorescence measurement, and protein chip, or at least one of the improved methods of the corresponding enzyme-linked immunoassays. Those different enzyme-linked immunoassays are different only in carrier, but they share the same reaction principle. After being subjected to anti-GP73 protein antibody concentration optimization treatment, those methods all can realize accurate quantitative detection and identification of a simple fatty liver and steatohepatitis in populations with fatty liver, and achieve the purpose of auxiliary diagnosis and treatment of steatohepatitis. The preparation of those GP 73 enzyme-linked immunoassays comes from mature enzyme-linked immunoassay preparation technologies, and those technologies were optimized to achieve excellent detection results.

In order to better explain the present invention, in certain embodiments of the present invention, the enzyme-linked immunoassay used for preparing the reagent was preferably enzyme-linked immunosorbent assay, the detection reagent prepared by enzyme-linked immunoassay was prepared with reference to the method disclosed in the related patented technology of BEIJING HOTGEN BIOTECH CO LTD, and the antibody was the anti-GP73 protein antibody described in Example 1.

The GP73 enzyme-linked immunoassay detection reagent (for 96 persons) consists of 5 bottles of GP73 standard; 1 anti-GP73 protein antibody coated plate (96 wells); 1 bottle of a horseradish peroxidase (HRP) labeled anti-GP73 protein antibody, 10 ml/bottle; 1 bottle of a chromogen solution A and 1 bottle of a chromogen solution B, 5 ml/bottle for each solution; 1 bottle of a stop solution, 5 ml/bottle; and 1 bottle of a wash solution (20 times concentrated), 50 ml/bottle.

1. Preparation of standard for GP73 enzyme-linked immunoassay detection reagent

The high-value GP73 antigen was diluted in a 2% BSA solution at different concentrations of 0, 20 ng/ml, 40 ng/ml, 100 ng/ml, and 250 ng/ml; the preservative procline 300 was added to reach a final concentration of 0.1%; the resultant solutions were filtered and sterilized, and respectively placed into 1.5 ml vials, 0.5 ml per vial under sterile conditions. And they were stored at 4° C.

2. Preparation of anti-GP73 protein antibody coated plate (96 wells)

The ELISA plate was a 12×8 or 8×12 detachable ELISA strip plate. The anti-GP73 protein antibody was diluted to 10 to 50 μg/ml with a 0.05 mol/L, pH 9.5 carbonate buffer, and thereafter the resultant solution was added into each well of the ELISA plate, 100 μl per well; adsorption was performed overnight; the plate was washed with a wash buffer (a PBST solution containing a 20 mmol/L PBS and a 0.5% TWEEN®-20 (Polysorbate 20), the pH of the wash buffer was 7.4), and then each well was blocked with 120 μl of blocking buffer (a 2% BSA, diluted in a PBST solution) overnight; the blocking buffer was discarded, and the plate was air-dried to obtain an anti-GP73 protein antibody coated plate (96 wells). The plate was vacuum-sealed and packaged with an aluminum foil bag for later use.

3. Preparation of horseradish peroxidase (HRP)-labeled anti-GP73 protein antibody (the whole process is protected from light)

5 mg of HRP was weighed, and 250 μl of ddH$_2$O was added to dissolve; 5 mg of NaIO$_4$ was weighed, and 250 μl of ddH$_2$O was added to dissolve, thereby formulating a solution having a concentration of 20 mg/mL; the NaIO$_4$ solution was added dropwise into the HRP solution while stirring; and the mixed solution was left at 4° C. to stand for 30 minutes. 5 ml of ethylene glycol was taken and dissolved in 25 μl of ddH$_2$O, and the mixture was added dropwise to the above mixed solution while stirring; the final HRP concentration was 10 mg/ml, and the resultant was left at room temperature to stand for 30 minutes.

The anti-GP73 protein antibody concentration was adjusted to about 5 mg/ml; the anti-GP73 protein antibody was mixed with HRP at a ratio of 1:4; and the mixture was dialyzed in a 50 mmol/L, pH 9.5 carbonate buffer for more than 6 hours, wherein the buffer was changed after the first two hours.

The reaction was terminated with freshly prepared 1 mg of a NaBH$_4$ solution, the resultant solution was shaken well, and left at 4° C. to stand for 2 hours; thereafter, the solution was shaken every half hour.

The solution was dialyzed overnight with a 10 mM, pH 7.2 PBS (0.01 mol/L Na$_2$HPO$_4$ and NaH$_2$PO$_4$ stock solutions were prepared in advance, and the two solutions were mixed into a PBS buffer according to the required pH), and the PBS was changed once.

The anti-GP73 protein antibody solution for which the HRP labeling had been completed was dialyzed overnight with a saturated ammonium sulfate solution, and then centrifuged at 12,000 rpm in an ultrafiltration tube to obtain a concentrated and purified HRP-labeled anti-GP73 protein antibody.

The HRP-labeled anti-GP73 protein antibody was diluted to a suitable working concentration with a buffer (20 mmol/L PBS) containing 10% fetal bovine serum. The recommended dilution concentration was ≥1:500. The resultant solution was divided and placed into bottles, 10 ml/bottle, and stored at 4° C.

4. Preparation of chromogen solution A: a phosphoric acid-citric acid buffer (50 mmol/L, pH 5.0) and a 3% hydrogen peroxide solution were used to prepare the solution, and the solution was divided and placed into bottles, 5 ml/bottle.

5. Preparation of chromogen solution B: a TMB (0.1 mg/ml) methanol solution divided and placed into bottles, 5 ml/bottle.

6. Preparation of stop solution: 2 mol/L H$_2$SO$_4$, divided and placed into bottles, 5 ml/bottle.

7. Wash solution (20 times concentrated solution): a PBS (pH 7.4) and a 1% TWEEN®-20 (Polysorbate 20) solution were used to prepare the solution, and the solution was divided and placed into bottles, 50 ml/bottle.

The GP73 standard, the anti-GP73 protein antibody coated plate, the HRP-labeled anti-GP73 protein antibody, the chromogen solution A, the chromogen solution B, 1 bottle of the stop solution, and the wash solution (20 times concentrated) were assembled as required into the GP73 enzyme-linked immunoassay detection reagent (for 96 persons).

Example 4

The method of using the GP73 enzyme-linked immunoassay detection reagent (for 96 persons) included the following main steps:

1. Preparation of wash buffer: The concentrated buffer was diluted 20 times with purified water for later use.

2. Preparation of standards: The standards included 5 different concentrations, which were respectively 0, 20 ng/ml, 40 ng/ml, 100 ng/ml, and 250 ng/ml.

3. Antigen-antibody reaction: 100 μl of sample diluent was added into each micro-well of the antibody coated plate, and then 10 μl of respective standards at different concentrations or the serum samples to be tested were added and incubated at 37° C. for 30 minutes; and the plate was then washed 4 times with the wash buffer.

4. Enzyme-linked reaction: 100 μl of the HRP-labeled anti-GP73 protein antibody solution was added to each well and incubated at 37° C. for 30 minutes, and then the plate was washed 4 times with the wash buffer.

5. Color reaction: 50 μl of the chromogen solution A and 50 μl of the chromogen solution B were added in this order to each well, and incubation was performed at 37° C. for 10 minutes; and then 50 μl of the stop solution was added to each well to end the reaction.

6. Colorimetry: the absorbance of the blank control well was assigned a value of zero, and a microplate reader was used to measure the average OD value at 450 nm; the absorbance of each well was recorded; and the average value of the OD values of standards in two wells was calculated.

7. Result calculation

1) Drawing of a standard curve: a standard curve of this measurement was drawn with the standard concentration as the abscissa and the average OD value of the standard measurements as the ordinate; the standard curve regression coefficient $R^2$ was calculated, and when $R^2 \geq 0.98$, this experiment was valid.

2) Calculation of the concentration of the samples to be tested: According to the OD values of the samples to be tested, the GP73 concentration was calculated based on the standard curve.

Example 5

The immunochromatography is at least one of up-conversion luminescence immunochromatography, latex immunochromatography, colloidal gold immunochromatography, luminescence immunochromatography, and quantum dot immunochromatography.

Preparation of GP73 immunochromatography detection reagent: the immunochromatography is at least one of up-conversion luminescence immunochromatography, latex immunochromatography, colloidal gold immunochromatography, luminescence immunochromatography, quantum dot immunochromatography, and improved methods of the corresponding immunochromatography methods. Those different immunochromatography methods are different only in labeling particle, but they share the same reaction principle. After being subjected to anti-GP73 protein antibody concentration optimization treatment, those methods all can realize accurate quantitative detection and identification of a simple fatty liver and steatohepatitis in populations with fatty liver, and achieve the purpose of auxiliary diagnosis and treatment of steatohepatitis. The preparation of those GP 73 immunochromatography methods comes from mature immunochromatography preparation technologies, and those technologies were optimized to achieve excellent detection results.

In order to better explain the present invention, in certain embodiments of the present invention, the immunochromatography used for preparing the detection reagent was preferably up-conversion luminescence immunochromatography, and the detection reagent prepared by up-conversion luminescence immunochromatography was prepared with reference to the method disclosed in the related patented technology of BEIJING HOTGEN BIOTECH CO LTD, and the antibody was the anti-GP73 protein antibody described in Example 1.

Preparation of GP73 Immunochromatography Detection Reagent

1. Coating

The anti-GP73 protein antibody was diluted to 2 mg/ml to serve as a T-line coating solution, and the goat anti-mouse IgG was diluted to 2 mg/ml to serve as a C-line coating solution. The T-line coating solution and the C line coating solution were coated on a nitrocellulose membrane by a film sprayer, and the membrane was air-dried to obtain a monoclonal antibody coated membrane strip.

2. Up-conversion luminescent particle (UCP) labeled antibody 10 mg of UCP particles were weighed and placed into a conical flask, and 10 ml of a 0.20 M PB solution at pH 7.2 was added to prepare a UCP particle suspension; then 0.5 to 2 mg of the anti-GP73 protein antibody was added, and anhydrous glutaraldehyde was added to reach a final concentration of 1%, and stirring was performed overnight at 37° C.; the solution was centrifuged at 12000 rpm, 4° C. for 15 min, and the supernatant was discarded; 10 ml of a 0.20 M PB solution at pH 7.2 was added to the UCP precipitate, and the mixture was pipetted and mixed; centrifugation was performed at 12000 rpm, 4° C. for 15 min, the supernatant was discarded, and the UCP precipitate was collected for later use.

3. Preparation of lyophilized binding pad for GP73 immunochromatography detection reagent The UCP precipitate was resuspended with 50 ml of a 0.20 M PB solution at pH 7.2 to prepare a UCP marker suspension; centrifugation was performed at 12000 rpm, 4° C. for 30 min, and the supernatant was discarded; 45 ml of a lyophilization solution (pH=7.20, 20 M PB, containing 2% BSA, and 3% sucrose) was added; the UCP marker suspension was added onto glass fibers at 2 to 5 cm²/ml, and the glass fibers were lyophilized for 11 h; the resultant lyophilized bonding pad was cut into long strips having a width of 1 cm width, which were the lyophilized binding pads for GP73 immunochromatography detection reagent.

4. Assembly of test strip

The nitrocellulose membrane, an absorbent paper, the bonding pad, and a sample pad were stuck in this order onto a bottom plate, and cut into 4.0 mm wide strips; then the strips were put into the bottom case of a plastic card, covered with the top case of the plastic card, and pressed firmly; desiccant was added and the product was sealed and packaged.

5. Preparation of sample diluent

The components of the sample diluent included a 0.20 M PB solution at pH 7.2, and a 1% TWEEN®-20 (Polysorbate 20) added thereto.

6. The assembled GP73 immunochromatography detection reagent strip and the sample diluent together constitute the GP73 immunochromatography detection reagent, which is suitable for use with the up-conversion luminescence immunoassay analyzers of UPT-3A series of BEIJING HOTGEN BIOTECH CO LTD.

Example 6

Preparation of samples for GP73 quantitative detection: all of the samples for detection were from clinical samples and had definite clinical diagnosis backgrounds, wherein the clinical diagnoses were all fatty liver backgrounds.

A total of 200 samples were clinically diagnosed with fatty liver backgrounds, including 63 serum/plasma samples which were liver disease progression samples diagnosed with steatohepatitis backgrounds (including liver fibrosis samples and liver cirrhosis samples caused by steatohepatitis, but not including samples from liver cancer patients; hereinafter simply referred to as steatohepatitis samples) and 137 fatty liver samples with a simple fatty liver.

Whole blood samples are not easy to be stored for long periods of time, and it is not suitable to establish long-term cohort samples for detection and analysis. No analysis of whole blood samples is made in the Examples described in the present invention, but the methods for detecting GP73 and the determination criteria thereof, which are suitable for GP73 detection in whole blood and improved based on the present invention, used for diagnosis and identification of a simple fatty liver and steatohepatitis in populations with fatty liver, are still considered to be within the scope of the present invention.

Example 7

The quantitative detection reagents of three methods, including the GP73 magnetic particle-based chemiluminescence detection reagent, the GP73 enzyme-linked immunoassay detection reagent, and the GP73 immunochromatography detection reagent were respectively used to detect 200 samples clinically diagnosed with fatty liver backgrounds, and the detection results were respectively summarized and analyzed.

1. Analysis of detection results of different methodologies

The absolute bias, the relative bias, and the linear correlation of the detection results respectively obtained by using the three reagents including the GP73 magnetic particle-based chemiluminescence detection reagent, the GP73 enzyme-linked immunoassay detection reagent, and the GP73 immunochromatography detection reagent were statistically analyzed to determine deviation among those different methodologies.

a. Absolute bias analysis: The absolute deviations of all samples were calculated according to the methods and standards specified in "NCCLS EP9-A: Method Comparison and Bias Estimation Using Patient Samples".

The maximum absolute deviation between the detection results of the 200 cases obtained by using the GP73 magnetic particle-based chemiluminescence detection reagent and those obtained by using the GP73 enzyme-linked immunoassay detection reagent was 20.08, which was less than 4 times of the average absolute deviation between the detection results of the 200 cases obtained by using the GP73 magnetic particle-based chemiluminescence detection reagent and those obtained by using the GP73 enzyme-linked immunoassay detection reagent, namely, 20.22. For the details, please see FIG. 1, a diagram showing the absolute bias between the detection results of 200 cases obtained by using the GP73 magnetic particle-based chemiluminescence detection reagent and the detection results of 200 cases obtained by using the GP73 enzyme-linked immunoassay detection reagent.

Figure 2:
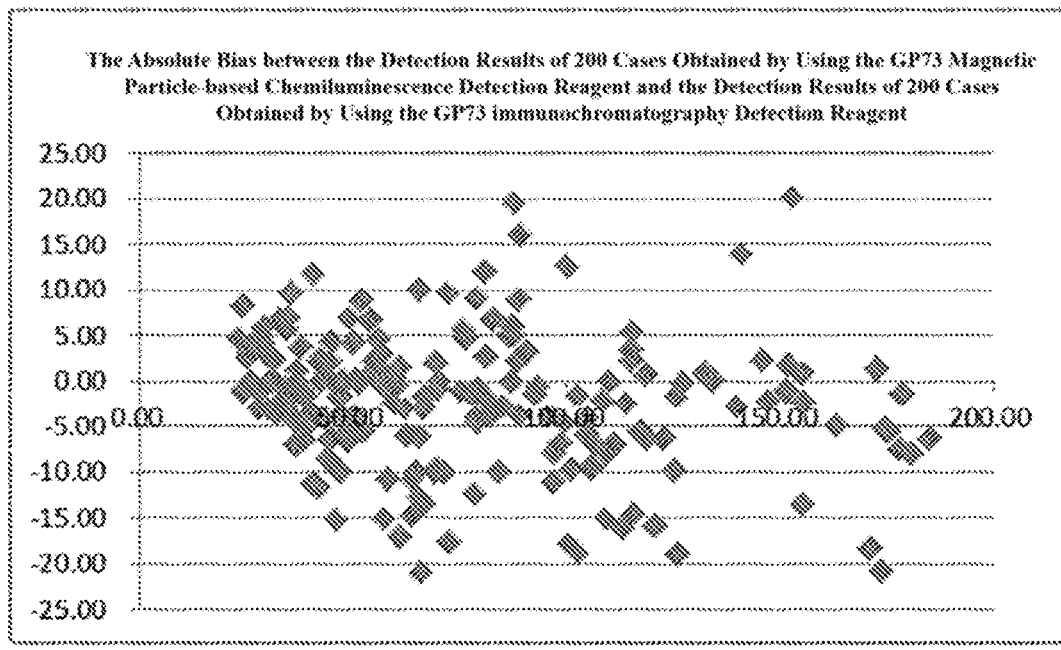
FIG. 2 is a diagram showing the absolute bias between the detection results of 200 cases obtained by using the GP73 magnetic particle-based chemiluminescence detection reagent and the detection results of 200 cases obtained by using the GP73 immunochromatography detection reagent.

The maximum absolute deviation between the detection results of the 200 cases obtained by using the GP73 magnetic particle-based chemiluminescence detection reagent and those obtained by using the GP73 immunochromatography detection reagent was 20.92, which was less than 4 times of the average absolute deviation between the detection results of the 200 cases obtained by using the GP73 magnetic particle-based chemiluminescence detection reagent and those obtained by using the GP73 immunochromatography detection reagent, namely, 20.10. For the details, please see FIG. 2, a diagram showing the absolute bias between the detection results of 200 cases obtained by using the GP73 magnetic particle-based chemiluminescence detection reagent and the detection results of 200 cases obtained by using the GP73 immunochromatography detection reagent.

Figure 3:
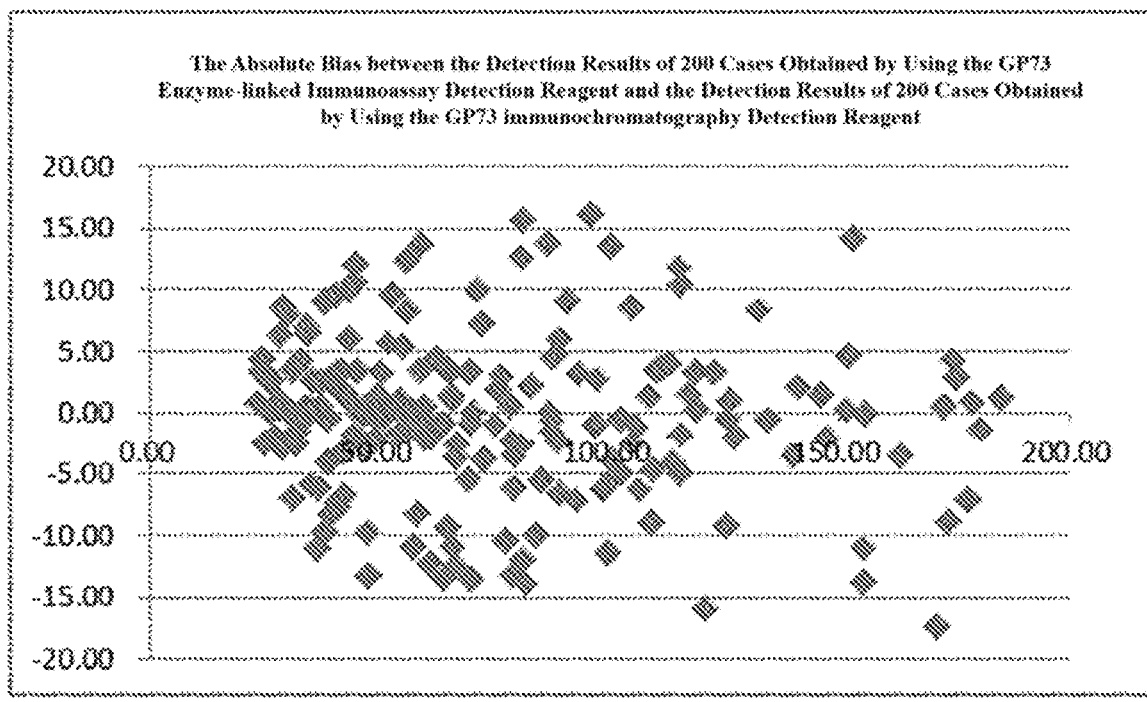
FIG. 3 is a diagram showing the absolute bias between the detection results of 200 cases obtained by using the GP73 enzyme-linked immunoassay detection reagent and the detection results of 200 cases obtained by using the GP73 immunochromatography detection reagent.

The maximum absolute deviation between the detection results of the 200 cases obtained by using the GP73 enzyme-linked immunoassay detection reagent and those obtained by using the GP73 immunochromatography detection reagent was 17.43, which was less than 4 times of the average absolute deviation between the detection results of the 200 cases obtained by using the GP73 enzyme-linked immunoassay detection reagent and those obtained by using the GP73 immunochromatography detection reagent, namely, 19.03. For the details, please see FIG. 3, a diagram showing the absolute bias between the detection results of 200 cases obtained by using the GP73 enzyme-linked immunoassay detection reagent and the detection results of 200 cases obtained by using the GP73 immunochromatography detection reagent.

According to the above analysis results, the absolute deviations among the detection results of the three reagents including the GP73 magnetic particle-based chemiluminescence detection reagent, the GP73 enzyme-linked immunoassay detection reagent, and the GP73 immunochromatography detection reagent all fell within the range specified by NCCLS EP9-A, so there was no significant deviation among the three methodologies.

b. Relative bias analysis: The relative deviations of all samples were calculated according to the methods and standards specified in "NCCLS EP9-A: Method Comparison and Bias Estimation Using Patient Samples".

Figure 4:
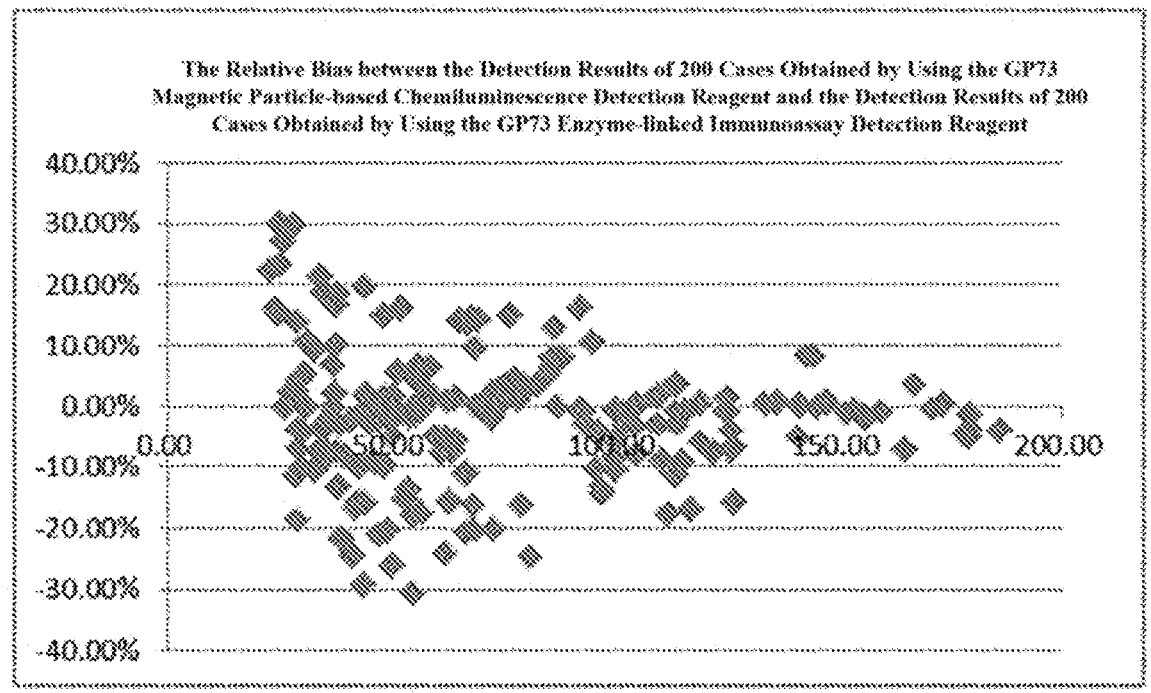
FIG. 4 is a diagram showing the relative bias between the detection results of 200 cases obtained by using the GP73 magnetic particle-based chemiluminescence detection reagent and the detection results of 200 cases obtained by using the GP73 enzyme-linked immunoassay detection reagent.

The maximum relative deviation between the detection results of the 200 cases obtained by using the GP73 magnetic particle-based chemiluminescence detection reagent and those obtained by using the GP73 enzyme-linked immunoassay detection reagent was 30.89%, which was less than 4 times of the average relative deviation between the detection results of the 200 cases obtained by using the GP73 magnetic particle-based chemiluminescence detection reagent and those obtained by using the GP73 enzyme-linked immunoassay detection reagent, namely, 32.36%. For the details, please see FIG. 4, a diagram showing the relative bias between the detection results of 200 cases obtained by using the GP73 magnetic particle-based chemiluminescence detection reagent and the detection results of 200 cases obtained by using the GP73 enzyme-linked immunoassay detection reagent.

Figure 5:
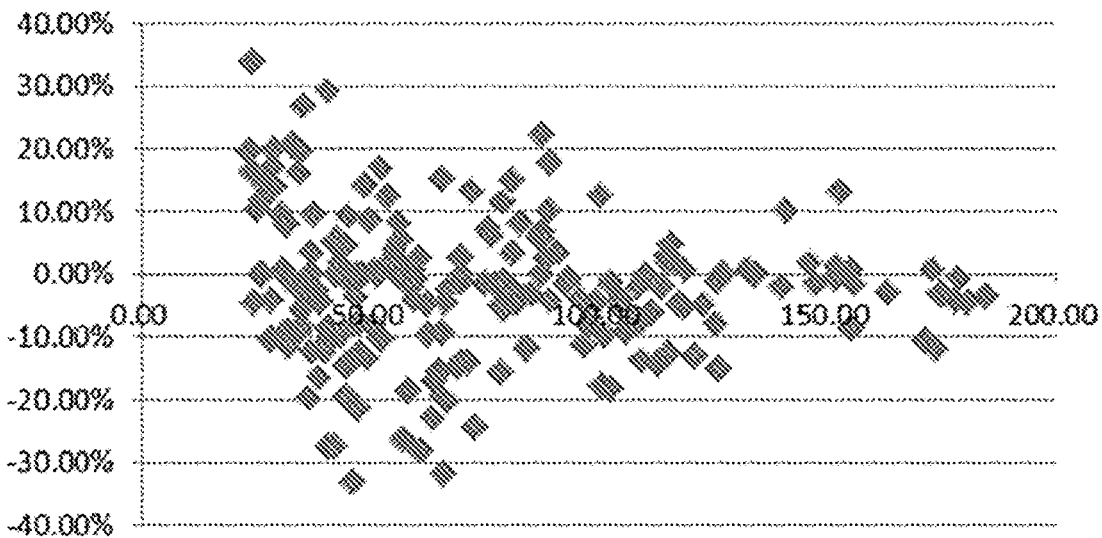
FIG. 5 is a diagram showing the relative bias between the detection results of 200 cases obtained by using the GP73 magnetic particle-based chemiluminescence detection reagent and the detection results of 200 cases obtained by using the GP73 immunochromatography detection reagent.

The maximum relative deviation between the detection results of the 200 cases obtained by using the GP73 magnetic particle-based chemiluminescence detection reagent and those obtained by using the GP73 immunochromatography detection reagent was 33.91%, which was less than 4 times of the average relative deviation between the detection results of the 200 cases obtained by using the GP73 magnetic particle-based chemiluminescence detection reagent and those obtained by using the GP73 immunochromatography detection reagent, namely, 33.98%. For the details, please see FIG. 5, a diagram showing the relative bias between the detection results of 200 cases obtained by using the GP73 magnetic particle-based chemiluminescence detection reagent and the detection results of 200 cases obtained by using the GP73 immunochromatography detection reagent.

Figure 6:
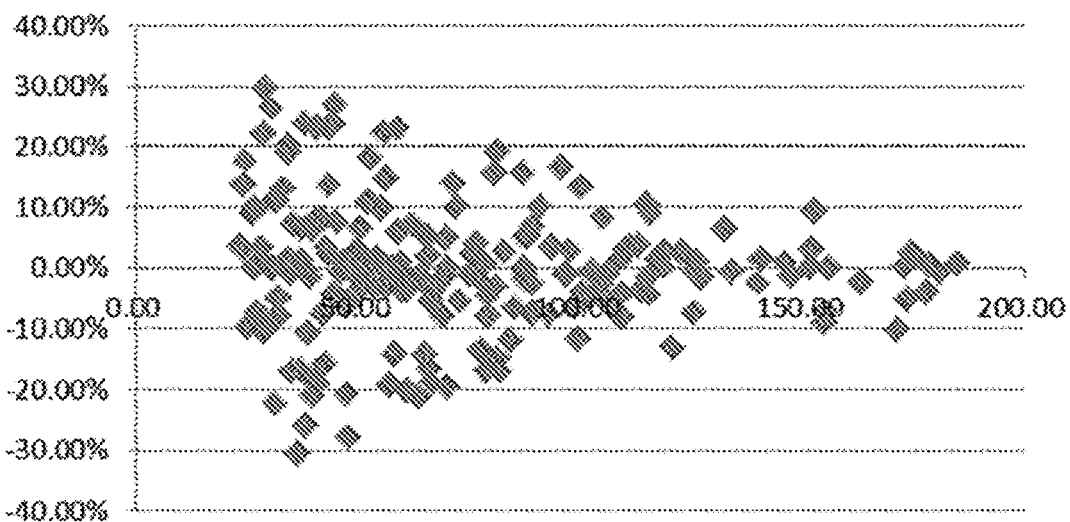
FIG. 6 is a diagram showing the relative bias between the detection results of 200 cases obtained by using the GP73 enzyme-linked immunoassay detection reagent and the detection results of 200 cases obtained by using the GP73 immunochromatography detection reagent.

The maximum relative deviation between the detection results of the 200 cases obtained by using the GP73 enzyme-linked immunoassay detection reagent and those obtained by using the GP73 immunochromatography detection reagent was 30.48%, which was less than 4 times of the average relative deviation between the detection results of the 200 cases obtained by using the GP73 enzyme-linked immunoassay detection reagent and those obtained by using the GP73 immunochromatography detection reagent, namely, 30.55%. For the details, please see FIG. 6, a diagram showing the relative bias between the detection results of 200 cases obtained by using the GP73 enzyme-linked immunoassay detection reagent and the detection results of 200 cases obtained by using the GP73 immunochromatography detection reagent.

According to the above analysis results, the relative deviations among the detection results of the three reagents including the GP73 magnetic particle-based chemiluminescence detection reagent, the GP73 enzyme-linked immunoassay detection reagent, and the GP73 immunochromatography detection reagent all fell within the range specified by NCCLS EP9-A, so there was no significant deviation among the three methodologies.

c. Linear correlation analysis

Figure 7:
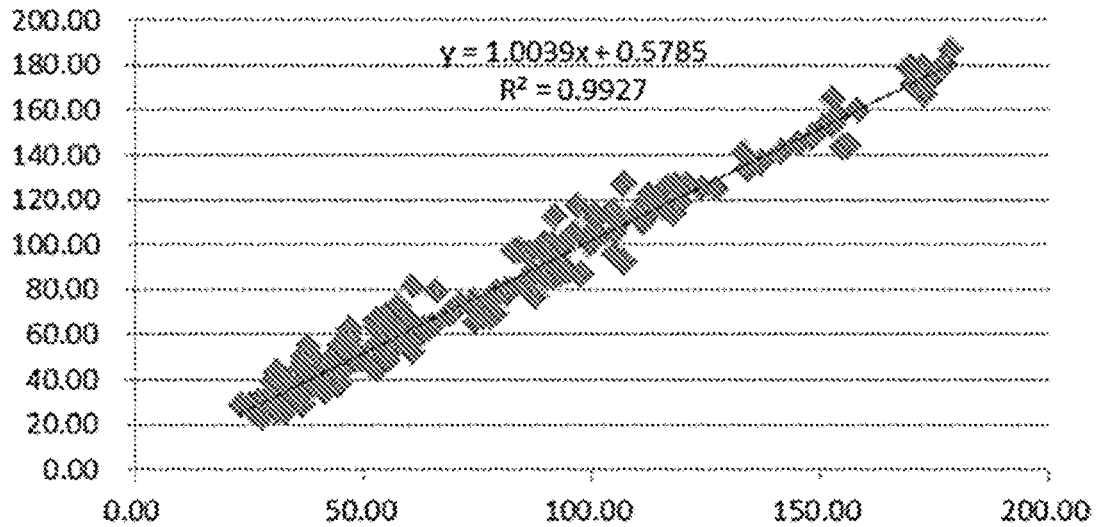
FIG. 7 shows a linear correlation between the detection results of 200 cases obtained by using the GP73 magnetic particle-based chemiluminescence detection reagent and the detection results of 200 cases obtained by using the GP73 enzyme-linked immunoassay detection reagent.

The correlation coefficient was calculated by using the software Graphpad Prism 4.0 based on the detection results of the 200 cases obtained by using the GP73 magnetic particle-based chemiluminescence detection reagent and the detection results of the 200 cases obtained by using the GP73 enzyme-linked immunoassay detection reagent: $R2=0.9927$. For the details, please see FIG. 7, which shows a linear correlation between the detection results of 200 cases obtained by using the GP73 magnetic particle-based chemiluminescence detection reagent and the detection results of 200 cases obtained by using the GP73 enzyme-linked immunoassay detection reagent.

Figure 8:
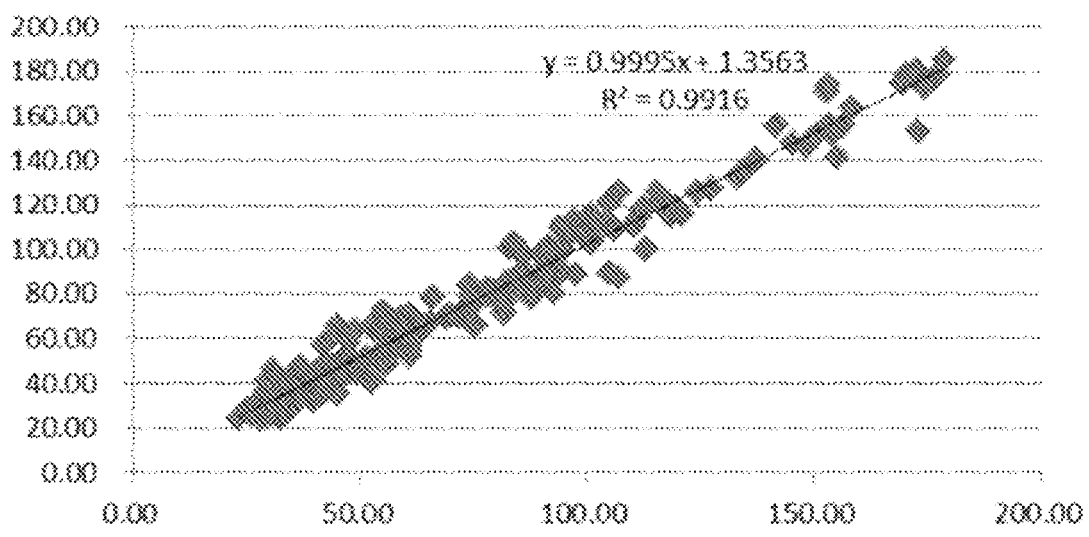
FIG. 8 shows a linear correlation between the detection results of 200 cases obtained by using the GP73 magnetic particle-based chemiluminescence detection reagent and the detection results of 200 cases obtained by using the GP73 immunochromatography detection reagent.

The correlation coefficient was calculated by using the software Graphpad Prism 4.0 based on the detection results of the 200 cases obtained by using the GP73 magnetic particle-based chemiluminescence detection reagent and the detection results of the 200 cases obtained by using the GP73 immunochromatography detection reagent: $R2=0.9916$. For the details, please see FIG. 8, which shows a linear correlation between the detection results of 200 cases obtained by using the GP73 magnetic particle-based chemiluminescence detection reagent and the detection results of 200 cases obtained by using the GP73 immunochromatography detection reagent.

Figure 9:
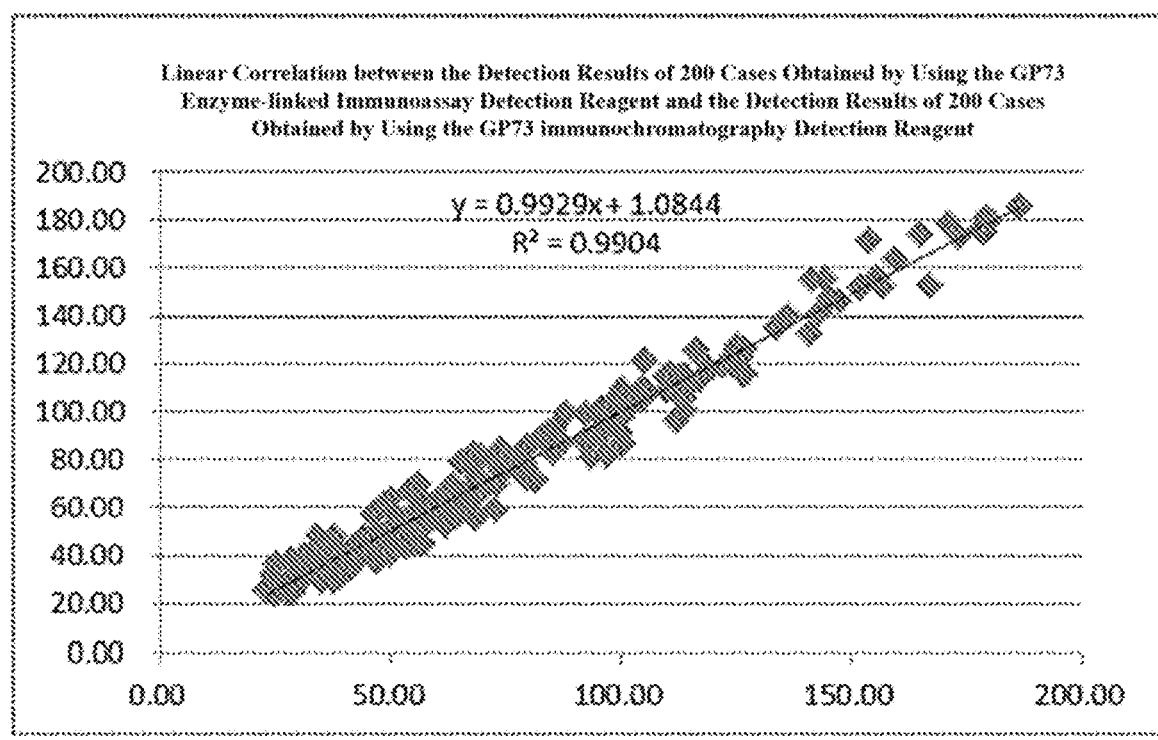
FIG. 9 shows a linear correlation between the detection results of 200 cases obtained by using the GP73 enzyme-linked immunoassay detection reagent and the detection results of 200 cases obtained by using the GP73 immunochromatography detection reagent.

The correlation coefficient was calculated by using the software Graphpad Prism 4.0 based on the detection results of the 200 cases obtained by using the GP73 enzyme-linked immunoassay detection reagent and the detection results of the 200 cases obtained by using the GP73 immunochromatography detection reagent: $R2=0.9904$. For the details, please see FIG. 9, which shows a linear correlation between the detection results of 200 cases obtained by using the GP73 enzyme-linked immunoassay detection reagent and the detection results of 200 cases obtained by using the GP73 immunochromatography detection reagent.

According to the results of the absolute bias analysis, the relative bias analysis, and the linear correlation analysis, when GP73 was employed for detection and analysis of fatty liver samples, the detection reagents adopting three methodologies, namely, the GP73 magnetic particle-based chemiluminescence detection reagent, the GP73 enzyme-linked immunoassay detection reagent, and the GP73 immunochromatography detection reagent had good consistency in regard to the detection results of fatty liver samples.

Figure 10:
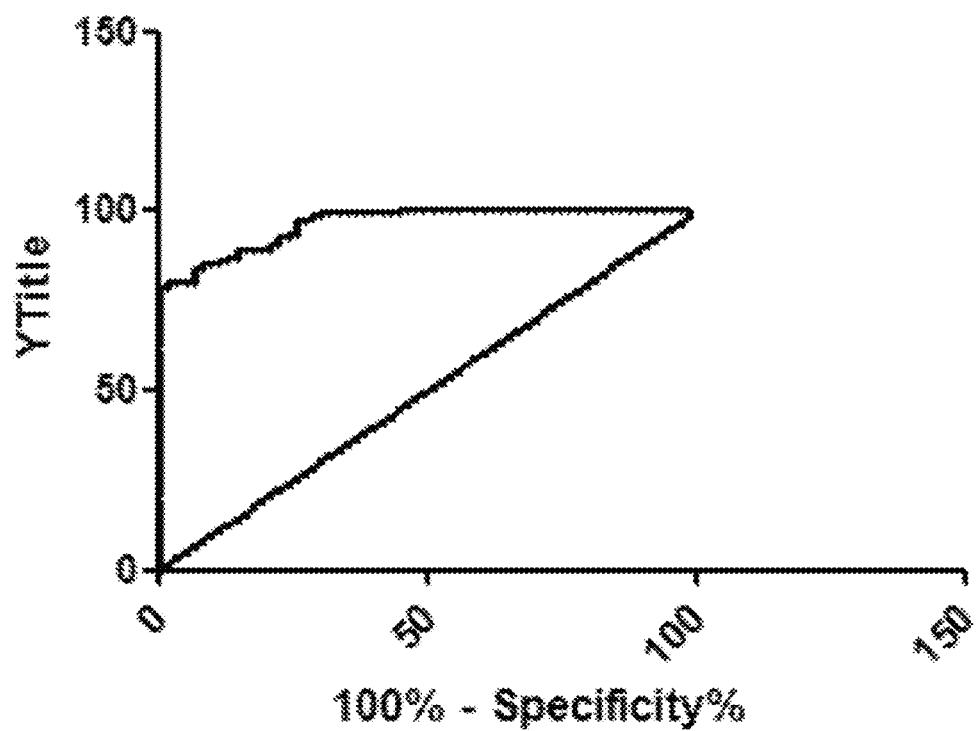
FIG. 10 is a ROC curve analysis chart.
Figures 11, 12:
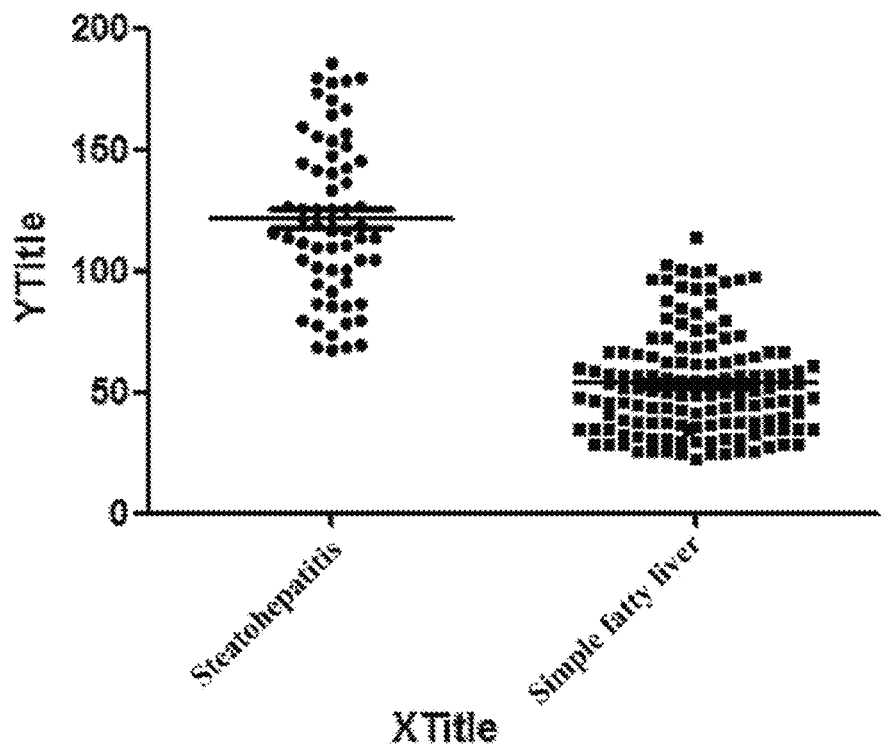
FIG. 11 is a diagram showing the data distribution of GP73 detection results.
FIG. 12 is a clinical consistency analysis chart.

4. Cut-off value setting and clinical consistency analysis of detection results a. Cut-off value setting:

Based on the analysis of the detection results of the GP73 magnetic particle-based chemiluminescence detection reagent and based on the 200 cases of clinical backgrounds, the cut-off value of GP73 for use in identification and diagnosis of a simple fatty liver and steatohepatitis in populations with fatty liver was 82.25 ng/ml according to the ROC curve analysis. For the details, please see FIG. 10, a ROC curve analysis chart; and FIG. 11, a diagram showing the data distribution of GP73 detection results.

b. Clinical consistency analysis

According to an analysis conducted by comparing the detection results with the results with known clinical background (137 cases of a simple fatty liver and 63 cases of steatohepatitis), by using a GP73 content of 82.25 ng/ml as the cut-off value for identifying and diagnosing a simple fatty liver and steatohepatitis in populations with fatty liver, the coincidence rate of a simple fatty liver was 86.86%, the coincidence rate of steatohepatitis was 85.71%, and the total coincidence rate was 86.50%. For the details, please see FIG. 12, a clinical consistency analysis chart. The deviation samples of which the clinical backgrounds did not coincident with the detection results were mainly concentrated within ±20% of the target value of 82.25 ng/ml.

According to the analysis of the Examples in the present invention, the serological target marker GP73 and application thereof can be used as an excellent serological target marker for identification and diagnosis of a simple fatty liver and steatohepatitis in populations with fatty liver; when a GP73 content of 82.25 ng/ml was used as a cut-off value for identifying and diagnosing a simple fatty liver and steatohepatitis in populations with fatty liver, the specificity was 86.86%, the sensitivity was 85.71%, and the test results among different detection methods have good consistency.

The serological target marker GP73 and application thereof are of high clinical application value for clinical identification and diagnosis of a simple fatty liver and steatohepatitis in populations with fatty liver, and for assisting in treatment of a simple fatty liver and steatohepatitis.

The above-mentioned Examples describe the preferred examples of the present invention. As mentioned above, it should be understood that they are illustrative of the present invention, rather than limiting the present invention to the forms disclosed in the Examples of the present invention. And they should not be considered to be exclusive of other examples, but can be used in various combinations and modifications of other forms, and can be changed within the scope of the concept of the present invention. Modifications and changes made by those skilled in the art within the concept and scope of the present invention shall all fall within the protection scope of the appended claims of the present invention.

What is claimed is:

1. A method for treating a human subject suffering from steatohepatitis, the method comprising:
    measuring a target marker GP73 in a blood sample to be tested from the human subject;
    comparing a measured value of the target marker GP73 in the sample to be tested with a standard value of the target marker GP73 thereof, the standard value being able to identify and diagnose steatohepatitis in populations with fatty liver;

identifying the human subject as suffering from a simple fatty liver in response to the measured value of the target marker GP73 in the sample to be tested is less than the standard value of the target marker GP73; and treating the human subject suffering from steatohepatitis with an anti-GP73 protein antibody.

2. The method according to claim 1, wherein the measurement is performed by an immunological method, which is any one selected from the group consisting of chemiluminescence, enzyme-linked immunoassay, and immunochromatography.

3. The method according to claim 2, wherein the chemiluminescence is at least one of magnetic particle-based chemiluminescence, electrochemiluminescence, time-resolved chemiluminescence, label enhanced chemiluminescence, or enzymatic chemiluminescence.

4. The method according to claim 2, wherein the enzyme-linked immunoassay is at least one of enzyme-linked immunosorbent assay, dot immunofiltration assay, magnetic particle-based enzyme-linked immunoassay, enzyme-linked immunofluorescence measurement, or protein chip.

5. The method according to claim 2, wherein the immunochromatography is at least one of up-conversion luminescence immunochromatography, latex immunochromatography, colloidal gold immunochromatography, luminescence immunochromatography, or quantum dot immunochromatography.

6. The method according to claim 1, wherein the sample to be tested is a serum sample or a plasma sample, from a population with fatty liver background.

7. The method according to claim 1, wherein the standard value of the target marker GP73 is a cutoff value of 82.25 ng/ml.

* * * * *